(12) United States Patent
Olejnik et al.

(10) Patent No.: US 6,306,426 B1
(45) Date of Patent: *Oct. 23, 2001

(54) IMPLANT DEVICE WITH A RETINOID FOR IMPROVED BIOCOMPATIBILITY

(75) Inventors: Orest Olejnik, Coto de Caza; Patrick M. Hughes, Aliso Viejo; John S. Kent, Newport Beach, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/587,485

(22) Filed: Jun. 5, 2000

Related U.S. Application Data

(63) Continuation-in-part of application No. 09/356,074, filed on Jul. 16, 1999, now Pat. No. 6,110,485, which is a continuation of application No. 09/150,990, filed on Sep. 10, 1998, now Pat. No. 6,074,661, which is a continuation of application No. 08/908,094, filed on Aug. 11, 1997, now abandoned.

(51) Int. Cl.[7] ............................... A61F 13/00; A61F 2/00; A61K 9/22
(52) U.S. Cl. .......................... 424/426; 424/422; 424/423; 424/424; 514/725; 514/953; 604/890.1
(58) Field of Search .................................... 424/422, 423, 424/424, 426, 427, 428; 514/725, 953, 954, 955; 604/890.1, 892.1

(56) References Cited

U.S. PATENT DOCUMENTS

| | | |
|---|---|---|
| 4,851,005 | 7/1989 | Hunt et al. .............................. 623/18 |
| 5,342,348 | 8/1994 | Kaplan .............................. 604/891.1 |
| 5,534,261 | 7/1996 | Rodgers et al. ...................... 424/450 |
| 5,554,181 | 9/1996 | Das .......................................... 623/1 |
| 5,562,922 | * 10/1996 | Lambert . |
| 5,733,565 | 3/1998 | Moo-Young et al. ............... 424/424 |
| 6,007,580 | 12/1999 | Lehto et al. ........................... 623/21 |

OTHER PUBLICATIONS

Giordano et al., Sustained Delivery of Retinoic Acid from Microspheres of Biodegradable Polymer in PVR, Invest. Ophthalmol. Vis. Sci., 34 (9) pp. 2743–2751 (1993)*

Kivalo et al., Biodegradable Tube Implants in Experimental Giaucoma Surgery in the Rabbit, Journal of Materials Science–Materials in Medicine v10, n1, pp. 53–58 (1999).*

* cited by examiner

Primary Examiner—Thurman K. Page
Assistant Examiner—Brian K. Seidleck
(74) Attorney, Agent, or Firm—Walter A. Hackler

(57) ABSTRACT

An implant device is provided which incorporates a retinoid for improving the biocompatibility of the device in tissue. The device may be bioerodible for the purpose of systemically or locally releasing a therapeutic agent in tissue or it may be a permanent implant which includes a surface treated with a retinoid for increasing the biocompatibility thereof.

10 Claims, 4 Drawing Sheets

IMPLANT DEVICE WITH A RETINOID FOR IMPROVED BIOCOMPATIBILITY

The present application is a continuation-in-part of U.S. Ser. No. 09/356,074 filed Jul. 16, 1999, now U.S. Pat. No. 6,110,485 which is a continuation of U.S. Ser. No. 09/150,990 filed Sep. 10, 1998, now U.S. Pat. No. 6,074,661 which is a continuation of U.S. Ser. No. 08/908,094 filed Aug. 11, 1997, now abandoned.

The present invention is generally related to implantable devices and is more particularly directed to an implantable prosthesis having improved biocompatibility. Still more particularly, the present invention is directed to an implantable device having improved biocompatibility while providing systemic release of a therapeutic agent in tissue.

It should be appreciated that physiological compatibility and biocompatibility are common problems for both implants for providing a systemic, or local, release of the therapeutic agent and for prosthesis, i.e., implants, utilized for functional or cosmetic reasons, or both.

It should be appreciated that the term "biocompatible" in the present application relates to a foreign object that can be left in a human or animal body for an extended or an indefinite period without causing any adverse physiological action.

The functional biocompatibility of an implant or device, is, of course, determined by the chemical and surface properties of the implant and its components. The general structure of a device, including mechanical strength, elasticity, flexibility, fatigue resistance, chemical inertness, impermeability to water, resistance to acid, etc., all contribute to biocompatibility which, of course, also depends upon the type of tissue into which the implant is to be inserted. Most importantly, the surface of the implant in contact with body tissues should also exhibit resistance to immunological attack, cell adhesion, pannus formation, etc.

Undesirable properties which can result from tissue interacting with the surface may significantly affect the efficiency of the implant and be counteractive to the intended use of the implant in certain medical devices, for example, sustained or controlled drug release devices.

The use of a sustained, or controlled release system has a well known advantage of providing an active agent at a relatively constant level of concentration in tissue. Sustained drug release systems have been utilized in a great number of applications including drug release into the vitreous for endophthalmitis and other vitreoretinal disorders with the use of antibiotics and a fungal agent, antineoplastic drugs and anti-inflammatory agents.

Unfortunately, in many instances, particularly where the implant is intended to remain in contact with tissue for extended periods of time, various problems associated with the physiological and chemical stability and compatibility with respect to various of the contacted tissues and biological fluids occurs. This is true even though the implant may function properly in its sustained or controlled release of the active agent.

For example, biomaterial such as a synthetic polymer, when contacted with blood, rapidly forms an adsorbed protein layer. Subsequently, conformational alterations and completing of proteins which may occur which activate defense mechanisms such as coagulation, platelet adhesion, and aggregation, white cell adhesion, etc.

In eye tissue, an implant may cause superficial vascularization of the cornea with infiltration of granulation tissue. Biodegradable polymers may cause mild foreign body reactions which include inflammation in the vitreous.

Implanted biomaterials will cause a typical foreign body reaction with fibrinous membrane formation. A fibrinous membrane will surround and encapsulate the implant. Contraction of this fibrous capsule can range from transient pain to serious sequelae depending upon the location. Fibrinous infiltration of the vitreous with a prominent inflammatory response can lead to traction retinal detachment, disruption of the retinal pigmented epithelium or breakdown of the blood retinal barrier. Tissue and organ adhesions may develop as a result of the fibrinous inflammation. Intraocular implants can also cause cataract formation. Iris-ciliary body adhesions would seriously effect the homeostasis of ocular tension. Implants, being foreign objects, may cause acute and chronic inflammation. Tissue necrosis and scarring may result as well as neovascularization. Biopolymers may often be antigenic and elicit allergic or other adverse events. In the case of an implantable material in the vasculature or heart thrombus formation and embolus may occur.

SUMMARY OF THE INVENTION

In accordance with one embodiment of the present invention, an implantable device is provided for systemic, or local, release of a therapeutic agent in tissue. The device generally includes a therapeutic agent along with a carrier sized for insertion into tissue in which the systemic release of a therapeutic agent is desired, the carrier including means for providing sustained or controlled release of the therapeutic agent.

In addition, retinoid means, present in the carrier, is provided for improving biocompatibility of the device in the tissue.

As will be described in detail hereinafter, this hereinbefore unrecognized property of a retinoid substantially reduces or prevents undesirable attributes which can result from tissue interacting with the surface of the implantable device.

More particularly, in accordance with the present invention, the retinoid means may comprise a retinoid receptor agonist and the therapeutic agent, carrier, and retinoid means, may be homogeneous. This homogeneity provides for ease of manufacturing through the use of simple extrusion techniques or injection molding.

Specifically, in accordance with this embodiment of the present invention, the means for providing time release of the therapeutic agent may comprise a biodegradable polymer, such as, for example, a poly(lactic acid) and poly(lactide-co-glycolide).

More particularly, in accordance with one embodiment of the present invention, the carrier may be sized for implanting into a sclera and the retinoid receptor agonist may be a retinoid acid, for example, selected from the group of naturally occurring retinoids such as Vitamin A (retinol), Vitamin A aldehyde (retinal), Vitamin A acid (retinoic acid) and their synthetic and natural congeners. These would include but not be limited to the isomers all trans; 9-cis; 11-cis; 13-cis; 9, 11-dicis, and 11, 13-dicis as well as physiologically compatible ethers, esters, amides and salts thereof. The 7, 8-dihydro and 5, 6-dihydro congeners as well as etretinate are also acceptable for the invention.

Compounds that intrinsically or upon metabolism possess the physiologic properties of retinoids are also included within the scope of this invention. These would include synthetic and natural retinoid compounds having affinity to nuclear retinoic acid receptors (RARs) and retinoid X receptors (RXRs).

More particularly, the retinoid receptor agonist may be ethyl-6-[2-(4,4-dimethylthiochroman-6-yl)ethynyl]

nicotinate, or 6-[2-(4,4-dimethylchroman-6-yl)ethynyl] nicotinic acid, or p-[(E)-2-(5,6,7,8-tetrahydro-,5,5,8,8-tetramethyl-2-naphthyl)propenyl]-benzoic acid.

Corresponding to the device of the present invention, a method in accordance with the present invention for improving biocompatibility of an implant in tissue generally includes the steps of providing a therapeutic agent, providing a carrier sized for insertion into tissue in which release of the therapeutic agent is desired, incorporating a therapeutic agent into a carrier in a manner enabling sustained or controlled release of the therapeutic agent and incorporating a retinoid into the carrier in an amount effective for improving biocompatibility of the carrier in the tissue.

Many conditions and diseases are treatable with stents, catheters, cannulae and other devices inserted into the esophagus, trachea, colon, biliary tract, urinary tract and other locations in the body, or with orthopedic devices, implants, or replacements. It would be desirable to develop devices and methods for reliably delivering suitable agents, drugs or bioactive materials directly into a body portion during or following a medical procedure, so as to treat or prevent such conditions and diseases, for example, to prevent abrupt closure and/or restenosis of a body portion such as a passage, lumen or blood vessel.

As a particular example, it would be desirable to have devices and methods which can deliver an antithrombic or other medication to the region of a blood vessel which has been treated by PTA, or by another interventional technique such as atherectomy, laser abllation, or the like. It would also be desirable that such devices would deliver their agents over both the short term (that is, the initial hours and days after treatment) and the long term (the weeks and months after treatment). It would also be desirable to provide precise control over the delivery rate fro the agents, drugs or bioactive materials, and to limit systemic exposure to them. This would be particularly advantageous in therapies involving the delivery of a chemotherapeutic agent to a particular organ or site through an intravenous catheter (which itself has the advantage of reducing the amount of agent needed for successful treatment), by preventing stenosis both along the catheter and at the catheter tip. A wide variety of other therapies could be similarly improved.

Another embodiment of the present invention includes an implantable device, specifically a surgically implantable prosthesis in combination with retinoid means for improving the biocompatibility of the prosthesis. More specifically, the retinoid means may be present in the form of a film on the prosthesis or, alternatively, bonded to a surface of the prosthesis.

Other implants to be considered as part of the present invention include biocompatible stents such as described in U.S. Pat. Nos. 5,342,348 and 5,554,381, biocompatible bone pins such as described in U.S. Pat. No. 4,851,005, biodegradable/biodegradable joint prosthesis such as described in U.S. Pat. No. 6,007,580, biodegradable birth control devices such as described in U.S. Pat. No. 5,733,565, biodegradable implants for treatment of prostate cancer or any biodegradable drug delivery system.

All of the hereinabove referenced patents are to be incorporated herewith, including all drawings and specifications, by this specific references thereto.

As hereinabove noted, the retinoid means may comprise a retinoid selected from the group of naturally occurring retinoids such as Vitamin A (retinol), Vitamin A aldehyde (retinal), Vitamin A acid (retinoic acid) and their synthetic and natural congeners. These would include but not be limited to the isomers all trans; 9-cis; 11-cis; 13-cis; 9, 11-dicis, and 11, 13-dicis as well as physiologically compatible ethers, esters, amides and salts thereof. The 7, 8-dihydro and 5,6-dihydro congeners as well as etretinate are also acceptable for the invention.

Compounds that intrinsically or upon metabolism possess the physiologic properties of retinoids are also included within the scope of this invention. These would include synthetic and natural retinoid compounds having affinity to nuclear retinoic acid receptors (RARs) and retinoid X receptors (RXRs).

Importantly, the present invention encompasses a method for improving biocompatibility of a surgically implantable prosthesis with the method comprising the step of combining a retinoid with the prosthesis. More particularly, the step may include disposing a film of retinoid on the prosthesis or, embedding retinoid, to the surface of the prosthesis. The retinoid may comprise a retinoid, as hereinabove noted, and be selected from the group of naturally occurring retinoids such as Vitamin A (retinol), vitamin A aldehyde (retinal), Vitamin A acid (retinoic acid) and their synthetic and natural congeners. These would include but not be limited to the isomers all trans; 9-cis; 11-cis; 13-cis; 9,11-dicis, and 11,13-dicis as well as physiologicelly compatible ethers, esters, amides and salts thereof. The 7, 8-dihydro and 5,6-dihydro congeners as well as etretinate are also acceptable for the invention.

Compounds that intrinsically or upon metabolism possess the physiologic properties of retinoids are also included within the scope of this invention. These would include synthetic and natural retinoid compounds having affinity to nuclear retinoic acid receptors (RARs) and retinoid X receptors (RXRs).

BRIEF DESCRIPTION OF THE DRAWINGS

The advantages and features of the present invention will be better understood by the following description when considered in conjunction with the accompanying drawings in which.

DETAILED DESCRIPTION

Figure 1:
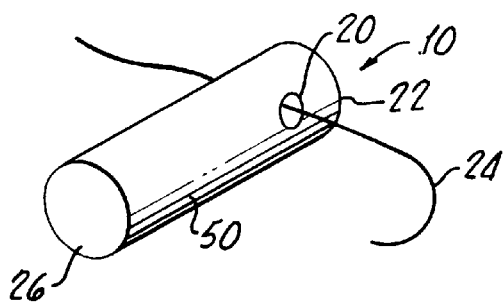
FIG. 1 is an implantable device in accordance with the one embodiment of the present invention, specifically a retinal plug, for providing local delivery to the intraocular tissues of a therapeutic agent.
Figure 2:
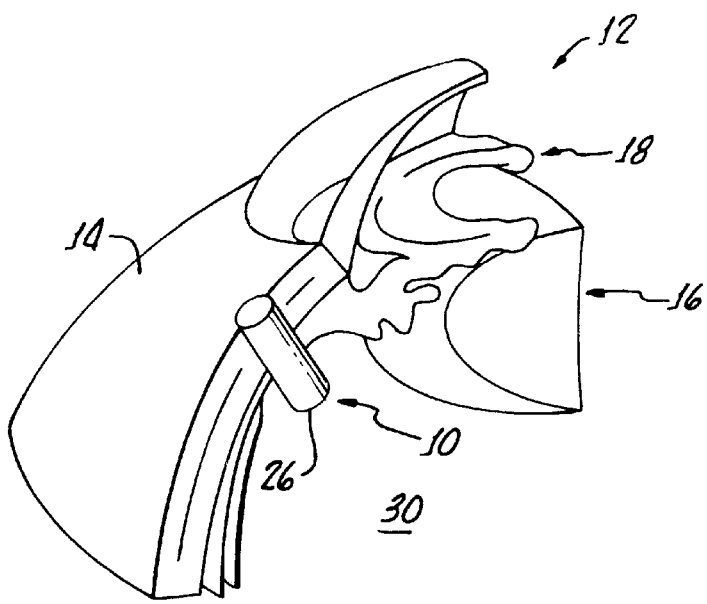
FIG. 2 is a diagram showing the positioning of the retinal plug shown in FIG. 1 in an eye through the sclera and pars plana.

Turning to FIGS. 1 and 2, there is shown an implantable device 10 for providing systemic release of a therapeutic agent in tissue. Device 10 is representative of a great number of devices for systemic release of a therapeutic agent. This specific embodiment 10 is a sterile, bioerodible plug for the intraocular delivery of pharmaceutically active compounds. Placement of the device 10 is illustrated in FIG. 2 as it may be inserted into an eye 12 specifically, the sclera 14 proximate the lens 16 and iris 18 for release of the drug into the sclera, choroid, retina and vitreous cavity. By way of example, the retinal plug, or device, 10, may have a weight of about 0.5 to about 10 milligrams, have a diameter of about 0.5 and about 2 millimeters and a length of between one and 12 millimeters. A hole 20 through a proximal end 22 of the device 10 enables a suture 24 to be used for securing the device 10, as shown in FIG. 2, with a distal end 26 thereof protruding into a vitreous cavity 30.

Any suitable therapeutic agent may be utilized. The diversity of therapeutic agents that can be delivered by the present invention is great and known to those skilled in the art. Examples include but are not limited to antibiotics, antifungals and antivirals such as erythromycin, tetracycline, aminoglycosides, cephalosporins, quinolones, penicilins, sulfonamides, ketoconazole, miconazole, acyclovir, ganciclovir, azidothymidine, interferon; anticonvulsants such as phenytoin and valproic acid; antidepressants such as amitriptyline and trazodone; antiparkinsonism drugs; cardiovascular agents such as calcium channel blockers, antiarythmics, beta blockers; antineoplastics such as cisplatin and methotrexate, corticosteroids such as dexamethasone, hydrocortisone, prednisolone, and triamcinolone; NSAIDs such as ibuprofen, salicylates indomethacin, piroxicam; Hormones such as progesterone, estrogen, testosterone; growth factors; carbonic anhydrase inhibitors such as acetazolamide; prostaglandins; antiangiogenic agents; neuroprotectants; other drugs known to those skilled in the art to benefit from controlled or sustained release from implantable devices or combinations thereof.

These active agents may be incorporated into a bioerodible polymer such as a poly ester, poly (ortho ester), poly (phosphazine), poly (phosphate ester), poly-caprolactone, poly (hydroxybutyric acid), natural polymer such as gelatin or collagen, or a polymeric blend. In addition, the present invention may also improve the biocompatibility of non-erodible polymeric implants.

Importantly, a retinoid is incorporated into the device 10 for improving the biocompatibility thereof. All of the components of the device 10 are extruded as a homogeneous system in the shape of a plug.

The device 10 may be optimized to resist sclera and choroidal erosion in order to prevent disintegration or fragmentation of the plug 10 into the vitreous cavity 30. This may be accomplished, as is well known in the art, by altering the surface, finish of the plug 10, coating the plug with another biodegradable semipermeable polymer, or the addition of another polymer to the blend. Because the plug is a homogeneous system, ease of manufacture is provided through simple extrusion techniques or injection molding.

The mechanism and rate of drug release may be controlled by the choice polymer, polymer molecular weight, polymer crystallinity, copolymer ratios, processing conditions, surface finish, geometry, excipient addition, and polymeric coatings, with the drug being released from the device 10 by diffusion, erosion, dissolution or osmosis.

The fabrication of various sclera plugs and the mechanism of controlling the drug release is well known in the art as set forth in numerous publications such as, for example, "Sclera Plug of Biodegradable Polymers for Controlling Drug Release in Vitreous", Mototane Hashizoe, Archophthalmol/ Volume 112, page 1380–1384, October, 1994; "A New Vitreal Drug Delivery Systems Using an Implantable Biodegradable Polymeric Device", Hideya Kimura et al, Investigative Ophthalmology and Visual Science, Volume 35, page 2815–2819, May, 1994, and U.S. Pat. No 5,466,233, all of which are incorporated herein in their entirety for the purpose of describing sclera plug manufacture, use and mechanisms.

All of the active ingredients utilized in the plug device 10 are present in a therapeutic effective amount which is calculated to achieve and maintain a therapeutic level in the vitreous cavity and introduced by the vitreous plug. Naturally, the therapeutic amount will vary with the potency of the active agent, the rate of release by the plug device 10.

The amount of incorporated retinoid will depend on the potency and receptor selectivity of the retinoid employed as well as the release rate of the retinoid from the specific implant. Typically, the amount of retinoid employed represents 0.001% to 50%, more typically from 0.01 to 20%.

Retinoic acid receptor agonists have been utilized for preventing proliferation of retinal pigment epithelium, see copending U.S. patent application Ser. No. 08/383,741, entitled "Method of Preventing Proliferation of Retinal Pigment of Epithelium by Retinoic Acid Receptor Agonists", filed in the name of Campochiaro and is to be incorporated herewith in its entirety for describing the use of retinoic acid activity in the vitreous cavity 30.

Figure 3:
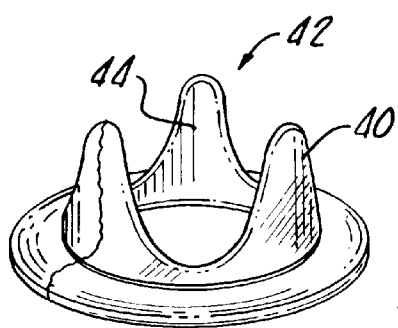
FIG. 3 is a perspective view of an alternative embodiment in accordance with the present invention, specifically a surgically implantable prosthesis such as a cardiac valve component coated with a film of retinoid.

Importantly, it has been discovered that the use of retinoids can improve the biocompatibility of the device 10 in tissue. While the retinoid may be incorporated into the device as a component of the homogeneous mass, as hereinabove described in connection with the plug device 10, the retinoid may also be used to advantage for improving biocompatibility when disposed as a film 40 on an implanted device 42 as shown in FIG. 3. The device 42 is a component for a cardiac valve as is described in U.S. Pat. No. 5,370,684 which is to be incorporated herewith in its entirety in describing typical implantable devices 42 suitable in combination with the retinoid for improving biocompatibility thereof. In addition, this patent is to be incorporated herein by the specific reference thereto for the purpose of coating or embedding techniques suitable for bonding the retinoid to the surface 44 of the implant 42.

When applied as a film 40 or imbedded into a surface 44 of the implant 42, the retinoid may be incorporated in amounts depending on the potency and receptor selectivity of the retinoid employed as well as the release rate of the retinoid from the specific implant.

Figure 4:
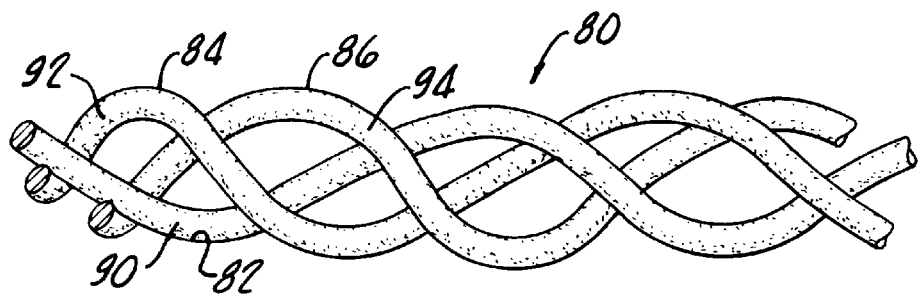
FIG. 4 is a perspective view of a stent coated with a film of retinoid.

With reference to FIG. 4 there is shown an endovascular stent 80 comprising a single helically wound strand 82 and a pair of counter-wound filaments 84, 86. Coatings 90,92,96 respectively disposed on the strand 82 and filaments 84, 86 improves the biocompatibility of the stent 80 as hereinabove described in connection with the implant 42 shown in FIG. 3. Alternatively, the retinoid may be embedded into the strand 82 and filaments 84, 86.

The stent 80 may provide delivery of therapeutic and other substances to a location within a patients' vascular system. (not shown)

The endovascular stent comprises a tubular structure having an initial diameter and being expandable from the initial diame ter to an enlarged diameter. The filaments 84, 86, providing a delivery matrix, are interlaced with the tubular structure and expandable therewith from the initial diameter to the enlarged diameter. A bioactive substance is releasably contained within the filament 84, 86 of the delivery matrix, and is released from said matrix when exposed to the conditions present in the vascular system.

The tubular structure may be composed of an elastic material, such as an elastomer polymer, whereby the tubular structure may be initially constrained to set initial diameter and thereafter released to said enlarged diameter, Alternatively, the tubular structure could be composed of a non-plastic material, whereby the tubular structure may be expanded from the initial diameter to the typically using a balloon dilatation catheter.

The various specific designs for the tubular structure exist, including a helical structure where the filament of the delivery matrix is counter woven with a helical strand of the tubular structure, a helical structure where the filament is laminated to a helically wound strand of the tubular structure, and a perforated cylinder where the filament of the delivery matrixes interwoven through perforations in the cylinder.

The filaments 84,86 of the delivery matrix may be porous and substantially non-erodible, where the bioactive substance is absorbed or impregnated therein and released over time. Alternatively, the filament will be composed of the material which is erodible within the vascular environment, where the bioactive substance is contained or dispersed in the filament and released as the filament material erodes. When an erodible material is used, the retinoid in incorporated therein as hereinabove described.

Figure 5:
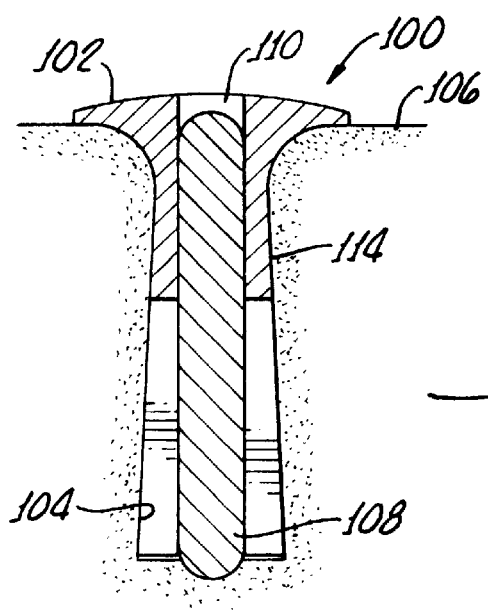
FIG. 5 is a cross section view of a stud implant coated with a film of retinoid.

With reference to FIG. 5 there is shown in sectional side elevation, a surgical implant kit 100 including a stud 102 disposed within a hole 104 drilled into a bone 106 with a pin 108 driven into a passage 110 through the stud 102. A retinoid coating 114 provides biocompatibility as hereinabove discussed.

Figure 6:
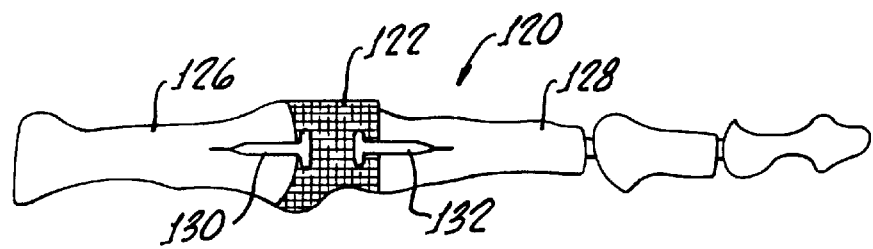
FIG. 6 in a side view of a joint prosthesis incorporating a retinoid in accordance with the present invention.

Turning to FIG. 6, there is shown a joint prosthesis 120 including a fibrous spacer 122 held in position between bones 126,128 to be joined by rigid fixation pins 130,132.

The spacer 122 may include a biodegradable polymer, co-polymermixture and/or composite such as described in U.S. Pat. No. 6,007,580 and including a retinoid as herein described to improve biocompatibility.

Typically, the amount of retinoid employed represents 0.001% to 50%, more typically from 0.01 to 20%.

The retinoid may be either naturally occurring or a synthetic retinoid such as a retinoic acid receptor (RAR) agonist.

Naturally occurring retinoids suitable for use in the present invention includes naturally occurring retinoids such as Vitamin A (retinol), Vitamin A aldehyde (retinal), Vitamin A acid (retinoic acid) and their synthetic and natural congeners. These would include but not be limited to the isomers all trans; 9-cis; 11-cis; 13-cis; 9,11-dicis, and 11,13-dicis as well as physiologically compatible ethers, esters, amides and salts thereof. The 7,8-dihydro and 5,6-dihydro congeners as well as etretinate are also acceptable for the invention.

Compounds that intrinsically or upon metabolism possess the physiologic properties of retinoids are also included within the scope of this invention. These would include synthetic and natural retinoid compounds having affinity to nuclear retinoic acid receptors (RARS) and retinoid X receptors (RXRs).

Other synthetically prepared retinoids are also well known in the art. For example, see U.S. Pat. No. 5,234,926 which is incorporated here by reference thereto in its entirety which discloses methods of synthesizing disubstituted acetylenes bearing heteroaeromatic and heterobicyclic groups with a selective activity as RAR agonists. U.S. Pat. No. 4,326,055 is incorporated herewith by reference thereto in its entirety for disclosing methods for synthesizing 5, 6, 7, 8-tetrahydro naphthal and indanyl stilbene derivatives with retinoid-like activity.

Examples of synthetic agonists suitable for use in the practice of this invention are ethyl 6-[2-(4,4-dimethylthiochroman-6-yl)ethynyl]nicotinate (Compound 168) and 6-[2-(4,4-dimethylchroman-6-yl)ethynyl]nicotinic acid (Compound 299), whose synthesis is disclosed in U.S. Pat. No. 5,234,926 as Examples 6 and 24, respectively; and p-[(E)-2-(5,6,7,8-tetrahydro-5,5,8,8-tetramethyl-2-naphthyl)propenyl]-benzoic acid (Compound 183), whose synthesis is disclosed in U.S. Pat. No. 4,326,055, and 2-[(E)-2-(5,6,7,8-tetrahydro-3,5,5,8,8-pentamethylnaphthaleen-2-yl)propen-1-yl]thiophene-4-carboxylic acid (Compound 701), whose synthesis is disclosed in U.S. Pat. No. 5,324,840, Example 11.

Alternatively, the sclera plug 10, while being generally homogeneous, may include a film 50 of retinoid thereon in order to improve biocompatibility in a manner similar to the improved biocompatibility of a non-bioerodible device 42 such as shown in FIG. 3.

Accompanying the hereinabove described devices is a method in accordance with the present invention for improving the biocompatibility of an implant in tissue which includes the step of providing a therapeutic agent, providing a carrier sized for insertion into the tissue in which the release of a therapeutic agent is desired, incorporating the therapeutic agent into a carrier in a manner enabling the time released of the therapeutic agent and incorporating the retinoid into the carrier in an amount effective for improving the biocompatibility of a carrier in the tissue. This method, of course, corresponds to the device 10 shown in FIGS. 1 and 2.

Correspondingly, a method in accordance with the present invention relating to the device 42 shown in FIG. 3 include combining the retinoid 40 with the prosthesis 42. This method may include the deposition of a film 40 on the prosthesis 42 or imbedding the retinoid into surface 44 of the prosthesis. All of the hereinabove recited retinoids may be used in accordance with the method of the present invention.

The following example illustrates the effectiveness of the method and devices of the present invention. It should be appreciated that the example is set forth herein for the purpose of illustration only and is not to be regarded as limiting to any of the specific materials or methods disclosed.

EXAMPLE 1

An implantable device 10 was prepared as follows:

Retinal plugs were manufactured from poly(D,L)lactic acid (PLA) with an intrinsic viscosity of 0.6 DL/G. The retinoid 6-[(4,4-dimethyl thiochroman-6-yl) ethynl] nicotinic acid (AGN190299) was mixed with polymer in a three-dimensional mixer. The mixture was then extruded at 85° C. into a homogeneous rod. The retinoid was incorporated into the polymeric plug at a concentration of 10%. The extruded plug was then cut to a length of 3.0 mm and had a diameter of 1.5 mm. A 0.5 mm hole was drilled into the distal end of the plug to allow for suture fixation to the sclera. Placebo plugs containing no retinoid were also manufactured to the same dimensions. The average weight of the plugs was 8 mg. All plugs were sterilized by gamma irradiation at 1 Mrad.

The plugs were then implanted into pigmented rabbits as shown in FIG. 2. The rabbit eyes were vitrectomized and the retinal plugs with or without incorporated retinoid were inserted through a sclerotomy 3 mm posterior to the corneoscleral limbus. The plugs were then fixated with the suture used to close the sclerotomy. An intravitreal injection of 500,000 human RPE cells was given to simulate traction retinal detachment. The rabbits were sacrificed at 28 days and histopathology was done.

Figure 7:
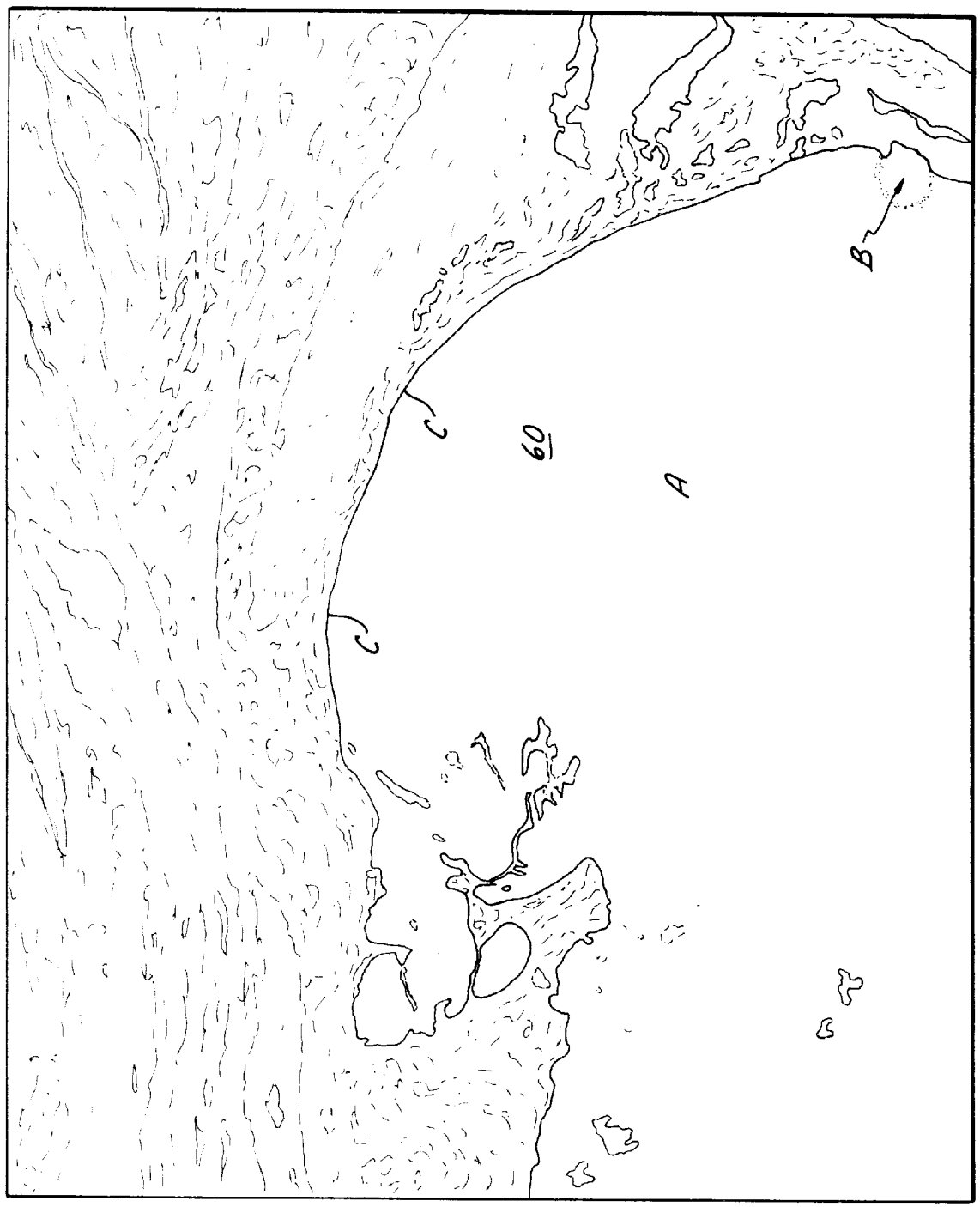
FIG. 7 is a drawing showing the encapsulation of a placebo plug 28 days after insertion into the vitreous through sclera. The plug is comprised of polylactic acid. The plug disappears during the processing of the eye (A). The tissues surrounding the plug were stained with PAS and show a fibrous capsule surrounding the area (B) where the placebo was previously located. The capsule that surrounded the polylactic acid plug shows a very prominent inflammatory response with inflammatory cell infiltration (C)

These observed results are shown in FIG. 7 for the placebo plug and in FIG. 8 for the plug 10 including the retinoid as hereinabove described.

FIG. 7 is a drawing showing the encapsulation of a placebo plug 28 days after insertion into the vitreous through the sclera. The plug is comprised of polylactic acid. The plug disappears during the processing of the eye (A). The tissues surrounding the plug were stained with PAS and show a fibrous capsule surrounding the area (B) where the placebo was previously located. The capsule that surrounded the polylactic acid plug shows a very prominent inflammatory response with inflammatory cell infiltration (C).

Figure 8:
FIG. 8 is a drawing showing the encapsulation of a retinoid containing plug 28 days after insertion. The polylactic acid plug contained 10% by weight of the retinoid 6-[(4,4-dimethyl thiochroman-6-yl) ethynyl] nicotinic acid (AGN 190299). The plug disappears in the processing of the eye (A). The tissues surrounding the retinoid containing plug were stained with PAS. The figure shows that the capsule surrounding the AGN190299 plug (B) has very little fibrous inflammation (C).

FIG. 8 is a drawing showing the encapsulation of a retinoid containing plug 28 days after insertion. The polylactic acid plug contain 10% by weight of the retinoid 6-[(4,4-dimethyl thiochroman-6-yl) ethynyl] nicotinic acid (AGN190299). The plug disappears in the processing of the eye (A). The tissues surrounding the retinoid containing plug were stained with PAS. The figure shows that the capsule surrounding the AGN190299 plug (B) has very little fibrous inflammation (C).

Although there has been hereinabove described a particular arrangement of implantable devices and methods in accordance with the present invention, for the purpose of illustrating the manner in which the invention may be used to advantage, it should be appreciated that the invention is not limited thereto. Accordingly, any and all modifications, variations or equivalent arrangements which may occur to those skilled in the art, should be considered to be within the scope of the present invention as defined in the appended claims.

What is claimed is:

1. An implantable device for providing systemic or local release of a therapeutic agent in tissue, the device comprising:

a therapeutic agent;
   a carrier sized for insertion into tissue in which systemic release of the therapeutic agent is desired, said carrier including means for providing controlled release of the therapeutic agent wherein said means comprises a biodegradable polymer; and
   a retinoid, separate from the therapeutic agent and homogeneously distributed throughout the device for improving biocompatibility of said device in said tissue.

2. The device according to claim 1 wherein said retinoid comprises a retinoid receptor agonist.

3. The device according to claim 2 wherein said therapeutic agent, carrier and retinoid are homogeneous.

4. The device according to claim 1 wherein said biodegradable polymer comprises a poly(lactic acid).

5. The device according to claim 1 wherein said biodegradable polymer comprises poly(lactide-co-glycolide).

6. The device according to claim 2 wherein said retinoid receptor agonist comprises a naturally occurring retinoid.

7. The device according to claim 2 wherein said retinoid receptor agonist is selected from a group consisting of Vitamin A (retinal), Vitamin A aldehyde (retinal), Vitamin A acid (retinoic acid) and their synthetic and natural congeners.

8. The device according to claim 2 wherein the retinoid receptor agonist comprises ethy-6-[2-(4,4-dimethylthiochroman-6yl) ethynyl]nicotinate.

9. The device according to claim 2 wherein the retinoid receptor agonist comprises 6-[2-(4,4-dimethylchroman-6-yl)ethynyl]nicotinic acid.

10. The device according to claim 2 wherein the retinoid receptor agonist comprises p-[(E)-2-(5,6,7,8-tetrahydro-5,5,8,8-tetramethyl-2naphthyl)propenyl]-benzoic acid.

* * * * *